United States Patent
Buss et al.

(10) Patent No.: US 7,240,743 B2
(45) Date of Patent: Jul. 10, 2007

(54) SOIL PROBE INSERTION ARRANGEMENT AND METHOD OF USE

(75) Inventors: Peter Buss, Wood Forde (AU); Michael Reginald Dalton, Ingle Farm (AU); Riccardo Angelo Leo Gatto, Gardeni (AU); James Dominic Buob, Mitcham (AU)

(73) Assignee: Sentek Pty Ltd, Stepney, South Australia (AU)

( * ) Notice: Subject to any disclaimer, the term of this patent is extended or adjusted under 35 U.S.C. 154(b) by 166 days.

(21) Appl. No.: 10/489,644

(22) PCT Filed: Oct. 4, 2002

(86) PCT No.: PCT/AU02/01355

§ 371 (c)(1),
(2), (4) Date: Mar. 15, 2004

(87) PCT Pub. No.: WO03/031963

PCT Pub. Date: Apr. 17, 2003

(65) Prior Publication Data

US 2004/0238217 A1    Dec. 2, 2004

(30) Foreign Application Priority Data

Oct. 5, 2001   (AU) .................................... PR8078

(51) Int. Cl.
*E21B 49/02*   (2006.01)
(52) U.S. Cl. .......................................... 175/58; 175/20
(58) Field of Classification Search .................. 175/20, 175/58, 405; 405/249, 257
See application file for complete search history.

(56) References Cited

U.S. PATENT DOCUMENTS

| 415,037 | A | * | 11/1889 | Gray .......................... 405/251 |
| 427,815 | A | | 5/1890 | Wolf |
| 870,752 | A | | 11/1907 | White |
| 3,712,121 | A | * | 1/1973 | Fletcher et al. ................. 73/84 |
| 4,156,332 | A | | 5/1979 | Thompson |
| 4,929,885 | A | | 5/1990 | Dishman |

(Continued)

FOREIGN PATENT DOCUMENTS

AU            655602         10/1991

*Primary Examiner*—David Bagnell
*Assistant Examiner*—Daniel P Stephenson
(74) *Attorney, Agent, or Firm*—Klauber & Jackson (57) ABSTRACT

This invention relates to probes used in the ground for the collection of data relating to soil conditions and in particular to a construction and method of insertion of probe bodies that will house such probes. A probe body insertion apparatus comprises a tool for forming an opening in the soil using a stabilization device that encourages the excavation of an opening that is orthogonal to the surrounding ground level and which is smaller in diameter than the soil probe body to be inserted. The inserted end of the probe body is formed with a hollow portion having an opening that is downwardly facing and adapted to slice away a portion of the prepared opening. The soil sliced away falls to the base of the prepared opening. The hollow portion of the inserted end of the probe body envelopes the loose soil but allows the probe body to be inserted to the desired depth. The slicing action provides a smooth interface between the soil and the outer surface of the probe body, which is preferable for proper working of sensors used inside the probe body to measure soil parameters.

8 Claims, 7 Drawing Sheets

U.S. PATENT DOCUMENTS

| | | | |
|---|---|---|---|
| 5,123,623 A * | 6/1992 | McNamara | 248/545 |
| 5,186,263 A * | 2/1993 | Kejr et al. | 175/20 |
| 5,418,466 A | 5/1995 | Watson et al. | |
| 5,419,211 A * | 5/1995 | Rodel et al. | 73/864.45 |
| 6,431,006 B1 * | 8/2002 | Henke et al. | 73/784 |
| 2002/0031405 A1 * | 3/2002 | Queen et al. | 405/249 |
| 2003/0082012 A1 * | 5/2003 | Clark | 405/249 |

* cited by examiner

SOIL PROBE INSERTION ARRANGEMENT AND METHOD OF USE

This invention relates to probes used in the ground for the collection of data relating to soil conditions and in particular to a construction and method of insertion of such probes.

BACKGROUND

By way of example only, the following description relates to the insertion of probes into the ground.

Probes used to measure soil conditions take many forms and use different techniques for measuring soil properties. Capacitor based techniques are well known and involve the positioning of a capacitor type sensor (typically a pair of conductive rings) at a predetermined depth in the soil to make the measurements using the surrounding soil as a dielectric medium. A soil probe will typically have three to six such pairs located at various depths within a probe housing so as to collect data that, once analysed, will provide a soil profile of moisture and/or salinity as well as other soil properties either immediately or at intervals of time.

In particular the depth and extent of moisture penetration into the soil is of interest as is also the uptake of moisture from the soil by crops over time.

Thus the probe must be located in the soil to at least the required depth of the lowest sensor element, which typically requires a probe length of about 600 to 700 mm to be fully inserted into the soil.

Most importantly, the probe when placed in the soil, should be completely surrounded only by undisturbed soil. The presence of air gaps adjacent to the outer wall of the probe will disadvantage the measurement process since the air and water that collects in those gaps may bias the readings or in the worst case make the readings unusable.

Air gaps can occur as a result of poor installation technique and poor equipment. More particularly, the forces required to insert the probe to an appropriate depth can accidentally displace the end of the probe to the sides of the opening and this can make the opening non-circular and leave gouges in the side of the opening that become gaps after full insertion of the probe or a probe body. The soil is thus discontinuous with the outer surface of the probe, and a gap or gaps will exist into which air and/or soil water can collect. In use a measurement probe is located in a probe body.

One way in which to attempt to overcome the problems associated with insertion resistance and lack of a tight fit is to make the opening in the soil deeper so that resistance at the end of the insertion process is not as great, or alternatively or in addition make the fit of the tube to the opening in the soil as dose as possible. However, even these measures are not always successful or sufficient, as (depending on soil type) more soil than anticipated can be dislodged from the sides of the opening as the probe is inserted, the soil immediately surrounding the probe body is unnecessarily compacted and eventually when the probe is inserted to its lowest point, it still sometimes does not attain the required depth.

Dislodged soil in the above circumstance drops to the bottom of the prepared opening and builds up to a level that can, even with compression from above, resist the insertion of the probe to the required depth.

The provision of a pointed end on the inserted probe does not always suffice to ensure the most appropriate insertion force or success in obtaining the required depth.

The above mentioned problems are not always experienced, but if probes need to be removed each season so that the soil can be tilled, in all likelihood, problems of the above nature will occur. This is particularly the case for probes used in the soils of vegetable crops which need to be moved often since those crops are best grown in well tilled and cultivated ground, and have relatively short growing cycles.

The invention to be described herein will minimise or eliminate the problems described above and will also be useful in the placement of probes that use other than capacitor based techniques. It may also be useful in the placement of posts and other elongate structures into the ground.

BRIEF DESCRIPTION OF THE INVENTION

In a broad aspect of the invention, a body for insertion into the ground consists of;

an elongate body having a head end and an inserted end wherein said inserted end has a downwardly facing opening that is coaxial to said elongate body that opens to a hollow portion of said elongate body.

In a further aspect of the invention the hollow portion is terminated along the length of the elongate body to form a head end chamber and an inserted end chamber in the body so that each chamber is physically separated from the other.

In a yet further aspect of the invention the downwardly facing opening is adapted for ease of insertion into a prepared opening in the ground.

In another aspect of the invention the peripheral edge of the downwardly facing opening of said hollow portion of the elongate body has a rim that has a peripheral edge that is chamfered on its inside to create a sharp edge on the outside edge of the rim, that during insertion into a prepared opening in the ground, removes a portion of the ground about the prepared opening such that the removed portion falls to the bottom of the prepared opening in the ground and which eventually enters the downwardly facing opening of the inserted end into the hollow portion of the elongate body.

In an aspect of the invention, fitting the inserted end to the head end of the body forms a portion of said elongate body.

In a further aspect of the invention a body insertion stabilising means is positioned over the ground adapted to maintain the entry position of the tool that creates the opening in the ground during the creation of that opening and when said stabilising means is also adapted to maintain the entry position of the body as it is inserted into the prepared opening.

In a yet further aspect, the invention is a method of inserting into the ground a support as described above, comprising the steps of a) creating a longitudinal opening in the ground having cross-sectional dimensions smaller than that of the support to be inserted and which is at least as deep as the length of said support to be inserted into the ground;

b) inserting the inserted end of the support into the opening, and in doing so removing a portion of the ground about the prepared opening and which falls to the bottom of the prepared opening in the ground and enters the downwardly facing opening of the inserted end and accumulates in the hollow portion of the elongate body of said support until the required depth of the support has been inserted.

A further step of the invention is c) positioning over the ground a support insertion stabilising means that maintains the entry position of the tool that creates the opening in the ground during the creation of that opening and which is also adapted to maintain the entry position of the support as it is inserted into the prepared opening.

A yet further aspect of the invention is the step of d) removing the support insertion stabilising means before the full insertion of the body so as to position the head end of the body as deep in said soil as adapted to do so.

Specific embodiments of the invention will now be described in some further detail with reference to and as illustrated in the accompanying figures. These embodiments are illustrative, and not meant to be restrictive of the scope of the invention. Suggestions and descriptions of other embodiments may be included within the scope of the invention but they may not be illustrated in the accompanying figures or alternatively features of the invention may be shown in the figures but not described in the specification.

DETAILED DESCRIPTION OF EMBODIMENTS OF THE INVENTION

Figure 1:
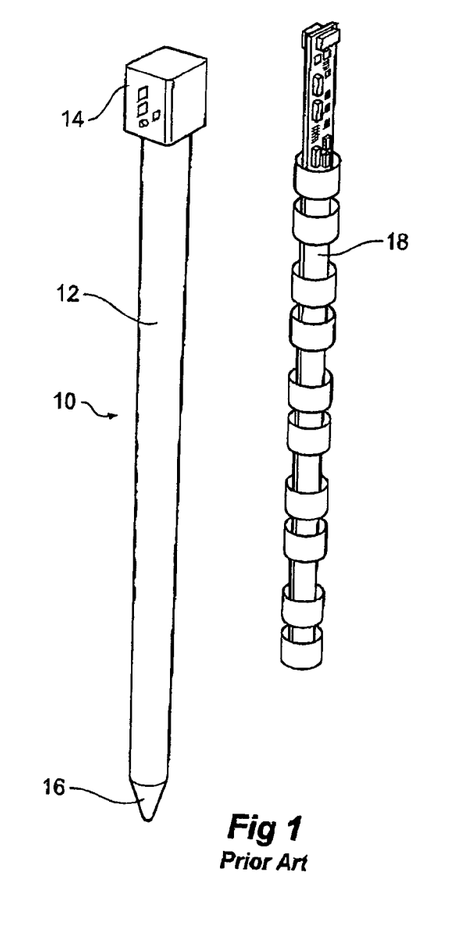
FIG. 1 depicts a prior art probe housing and adjacent to it a circuit board on which are arrayed pairs of conductive rings of a size to fit inside the probe housing.

FIG. 1 depicts a prior art probe housing or body 10 that is cylindrical and elongate having a head end 12 terminated by a cover 14, and a conical (pointed) inserted end 16. FIG. 1 also depicts an example of the sensor array 18 used inside the probe body and which is useable in the probe body of the invention.

This specification describes the use of a cylindrical (circular cross-section) probe body. This is not meant to be limiting as to the scope of the invention because the principles disclosed are applicable to various cross-sectional shapes and lengths of supports, and in the example used, probes, to be inserted in the ground.

It is however reasonable to expect that circular cross-section soil augers will be commonly available to create a suitable opening in the ground and because such soil augers are relatively simple for one person to operate for most ground conditions, such a combination is advantageous.

Alternative embodiments may well be possible but may require the use of additional powered mechanical excavation apparatus if large diameter probes or other shapes are to be used.

Minimum disturbance of the soil surrounding and immediately adjacent to the probe location is highly desirable as compaction in the vicinity may result in the measurements of the sensors used with the probe body not being applicable to the surrounding soil properties.

In this embodiment, the sensors are pairs of conductive rings arranged to accumulate electric charge the quantity and nature of that charge being affected by the dielectric characteristics of their surroundings. The use of a sensor of this type is but one of a number of alternative sensor types available. However, it is known that such sensors are very prone to the adverse effects of the existence of gaps in the soil in close proximity to the probe body where those gaps are occupied by air or water.

The applicant in this matter is the beneficial owner of Australian Patent No. 655602 entitled "MOISTURE AND SALINITY SENSOR AND METHOD OF USE" which was filed and granted in the names of at least one of the inventors of this invention. The body and figures of that specification are incorporated by reference into this specification. However, it is not an admission nor can it be assumed that the content of that specification has entered or comprises any part of the common general knowledge of this art in Australia or elsewhere as at the date of the filing of this specification.

In the above-mentioned incorporated specification, the operation of the conductive rings or sensor elements is disclosed. Suffice to say that when the term "sensor elements" is used in this specification, it could refer to pairs of conductive rings as will be used if capacitor based techniques are used, or other types of sensor devices suitable for operation while within the probe body.

It should also be noted that the sensor elements need not permanently reside within the probe body, but may be inserted by a user at predetermined times or intervals at which time measurements are performed. Measurements and relevant data collected are then collated and analysed elsewhere or on the spot with a portable typically handheld data processing device.

As stated previously, the insertion of the prior art probes and probe bodies is problematic as a result of variable insertion techniques and difficulties in repeating the desired results. There also exists an increased likelihood of the occurrence of insertion problems, which can be detrimental to the short and long-term accuracy of measurements taken by sensors located in the probe housing.

Figure 2:
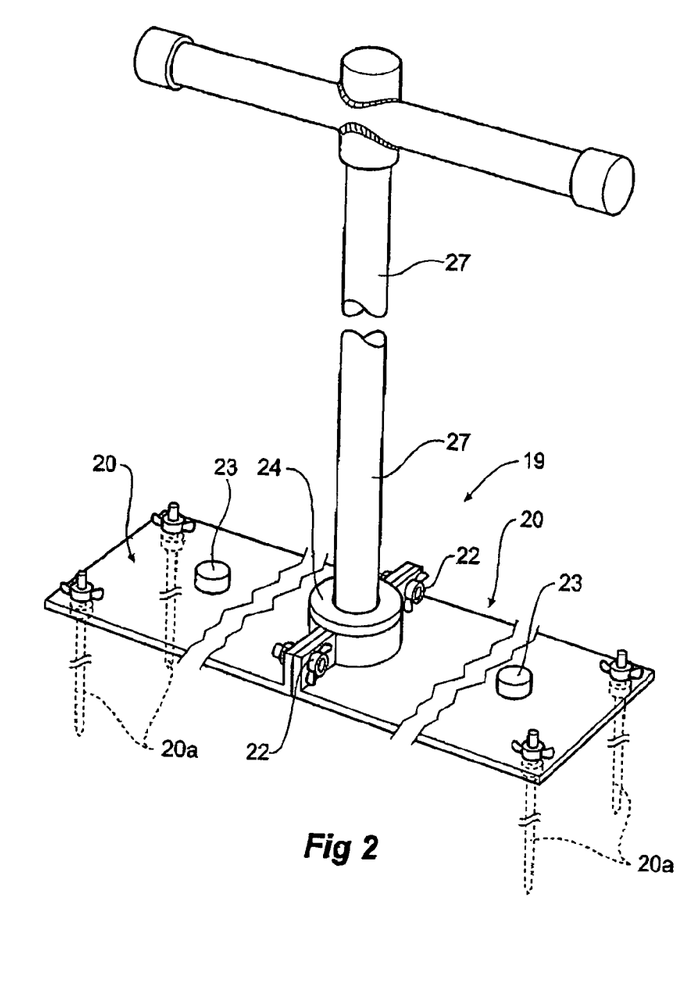
FIG. 2 depicts a probe housing insertion stabilising means and a hand operated auger.

FIG. 2 depicts an auger and probe body insertion stabilisation device 19 comprising two separable plates 20 that are firstly joined and positioned on the surface of the ground. The plates 20 are joined together by wing nuts 22 or other means about a circular aperture at the join of the plates. The joined plate is fixed into position over/on the ground by pegs 20a (as also shown in use in FIGS. 4 and 5) placed through apertures in the outside (with respect to the centre of the apparatus) ends of the plates. It is preferable to have the holes in the soil created by the pegs, a distance of about 30 cms from the location of the installed probe body. The holes created in the soil when the pegs are extracted from the soil following installation of the probe body may otherwise, if installed closer, create a gap in the soil surrounding the probe that could adversely affect any measurements made by the sensors installed in the probe body.

The clearance distance used is largely determined by the extent of the field of influence of the sensor. The smaller the field of influence the closer the pegs can be. In circumstances requiring positioning of the probe housing on a hill of soil located between formed furrows (eg as is common in vegetable crops) the pegs 20a are provided with sufficient length to stabilise the device 19. In one example, the upper ends of the pegs 20a are fixed to the plate which itself is then tapped downwards, using tapping buttons 23 on each plate, so as to force the pegs into the ground. Once the plate is flush with the upper surface of the hill of the cultivated soil the tapping is halted and the plate is ready to accept the auger. The circular aperture without the collar has an inner diameter that is the same as the outer diameter of the probe body to be inserted in the ground. Alternatively, the plates 20 may be joined after they are tapped into the soil.

FIG. 2 also depicts a collar 24 that has an outer diameter the same as the inner diameter of the circular aperture in the plates and an inner diameter the same as the outer diameter of a soil auger 27. The auger 27 is used to create an opening of lesser diameter than the soil probe body to be inserted.

With the auger and probe insertion stabilisation device 19 in place, the soil auger 27 can be kept upright while it is being used in the creation of an opening in the soil. Preferably the opening in the soil has a uniform inner diameter and its longitudinal axis is preferably orthogonal to the soil surface or at least the plane of the auger and probe stabilisation device.

Figure 3:
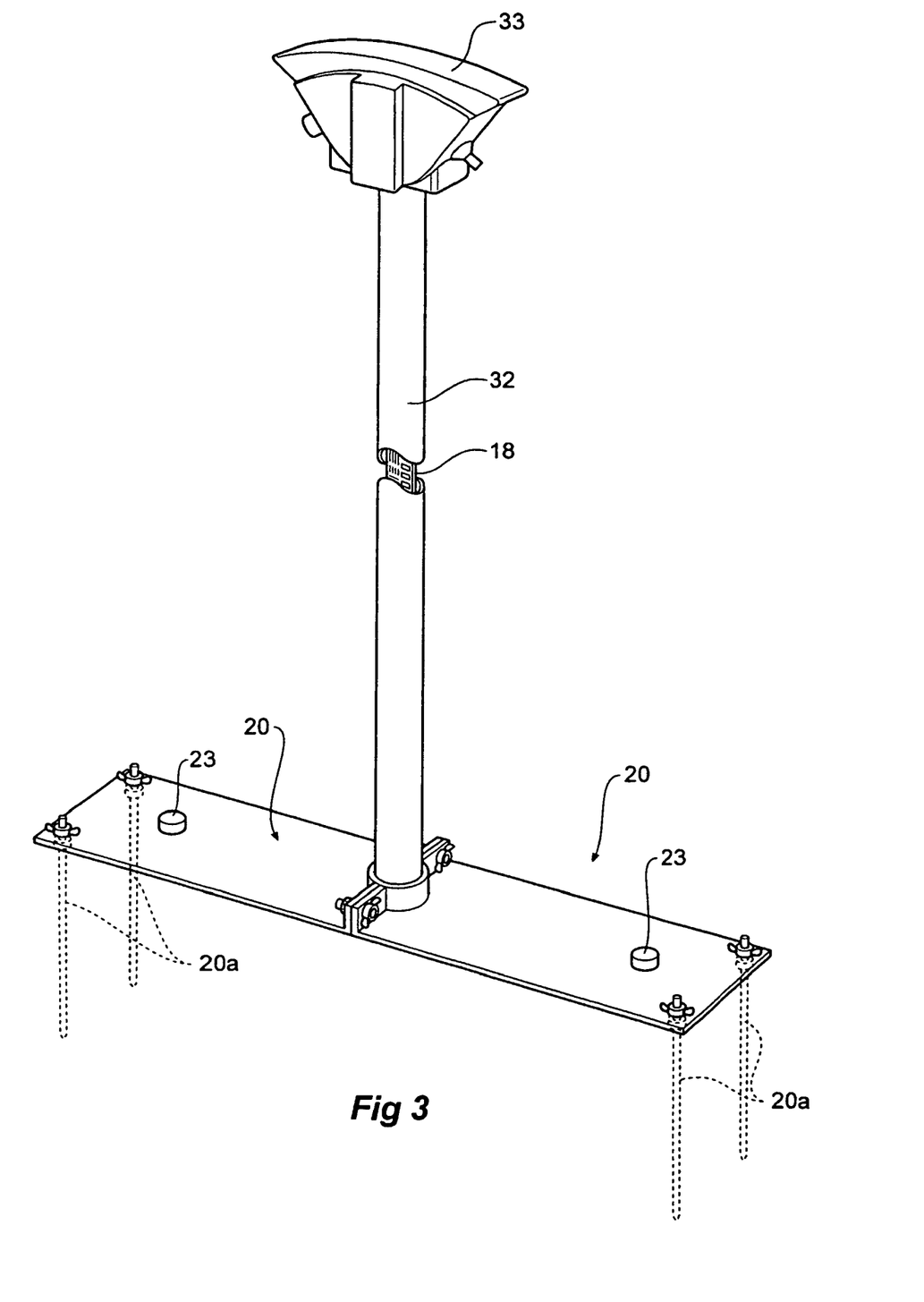
FIG. 3 depicts a closer perspective view of the stabilising means of FIG. 2 with a probe housing being inserted into the prepared hole.

FIG. 3 depicts a view of a probe body 32 partially inserted into the circular aperture between the plates that is created by the removal of the collar 24 (see FIG. 2). The preferred probe body head 33 is depicted and as shown is designed for ease of attachment of the cable or cables that provide a communications path for data and power to and from the sensor array 18 which is positioned inside the probe body.

Figure 4:
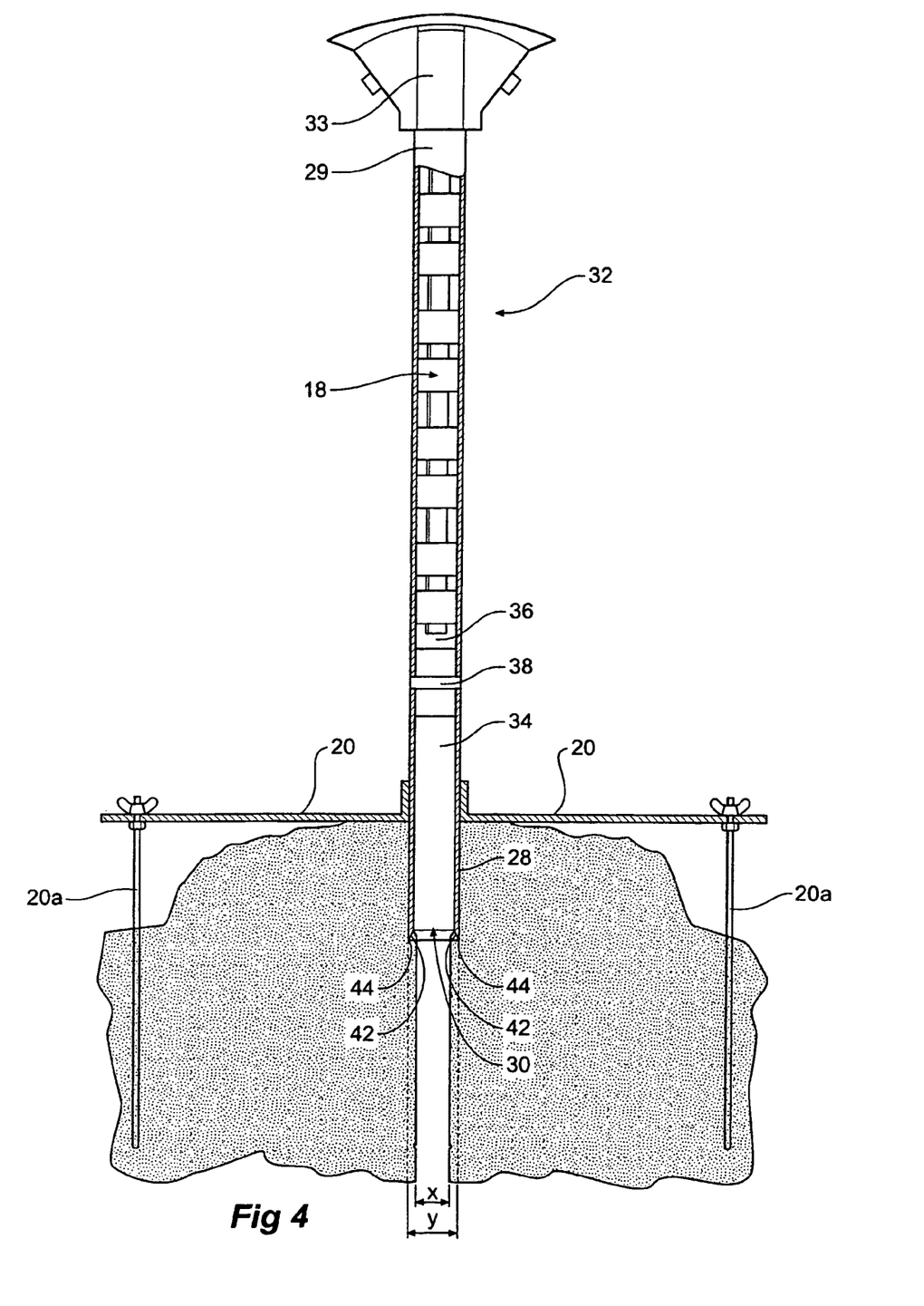
FIG. 4 depicts a cross-sectional view of the action of the insertion end of the probe housing being as it is inserted into the prepared opening in the ground.

FIG. 4 depicts the beginning of the probe body insertion process, showing in particular the inserted end 28 of the probe body having an opening 30 that faces downwardly with respect to the head end 29 of the probe body. Although the opening is shown in longitudinal cross-section the opening is circular in plan cross section and coaxial with the longitudinal axis of the elongate body of the probe body 32.

The probe body 32 has two distinct chambers 34 and 36, one being internal to the inserted end 28 and the other internal to the head end 29 of the probe. A barrier between the chambers 34 and 36 is provided, in this embodiment, by a joiner 38 which snugly fits its opposite ends into the bottom of the head end 29 and the top of the inserted end portions of the probe body.

The barrier formed by the joiner 38 prevents ingress of soil and moisture from the lower chamber 34 entering the upper chamber 36. Chamber 36 is the location within which the sensor array 18 and associated electronics reside in the probe body. The preferred three-part construction of the probe body comprising a joiner 38 located between the head end and inserted ends is but one way of the many ways for creating chambers 34 and 36 that will be apparent to those skilled in the relevant art.

Figure 5:
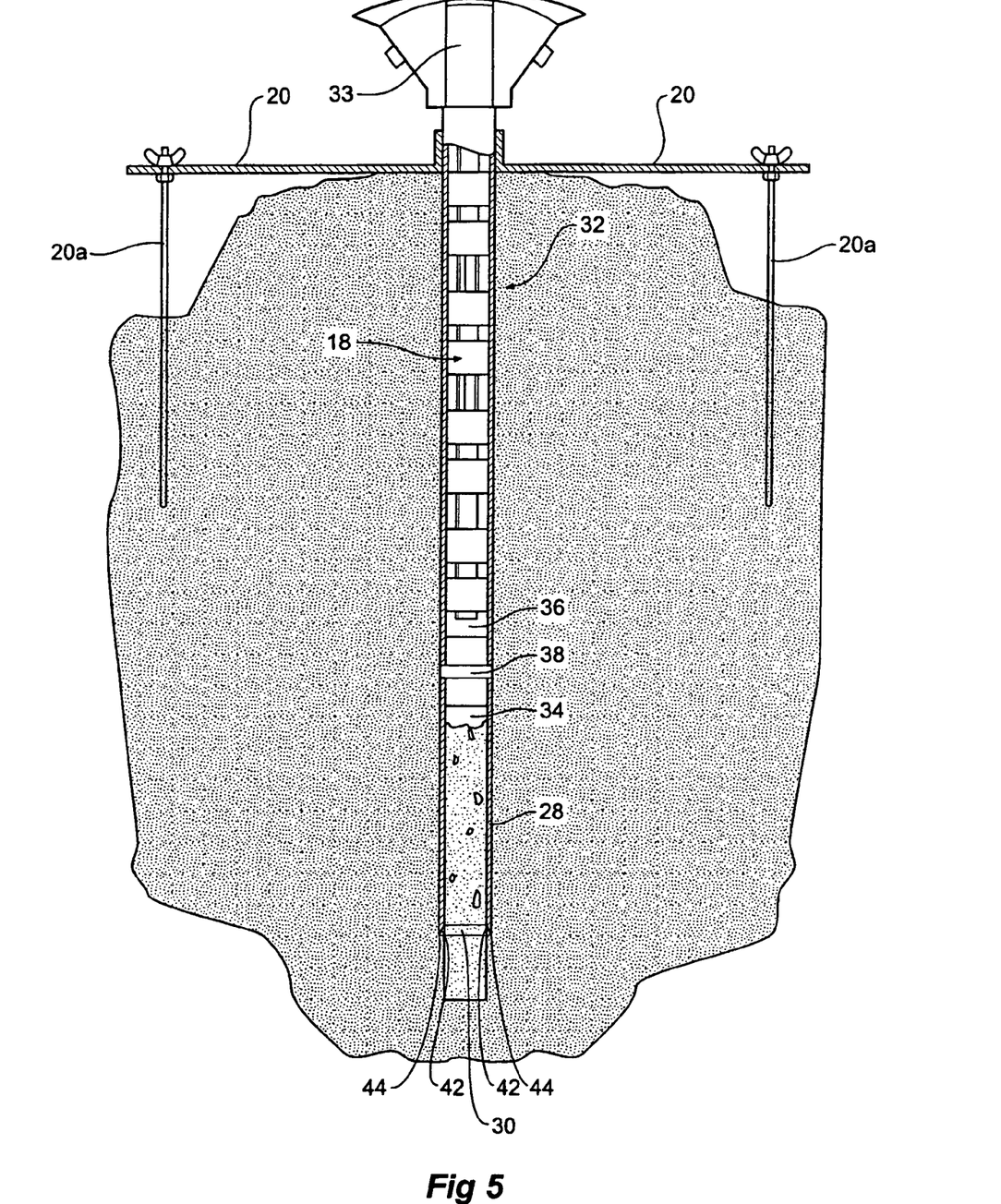
FIG. 5 depicts the almost fully inserted probe housing of FIG. 4.
Figure 7:
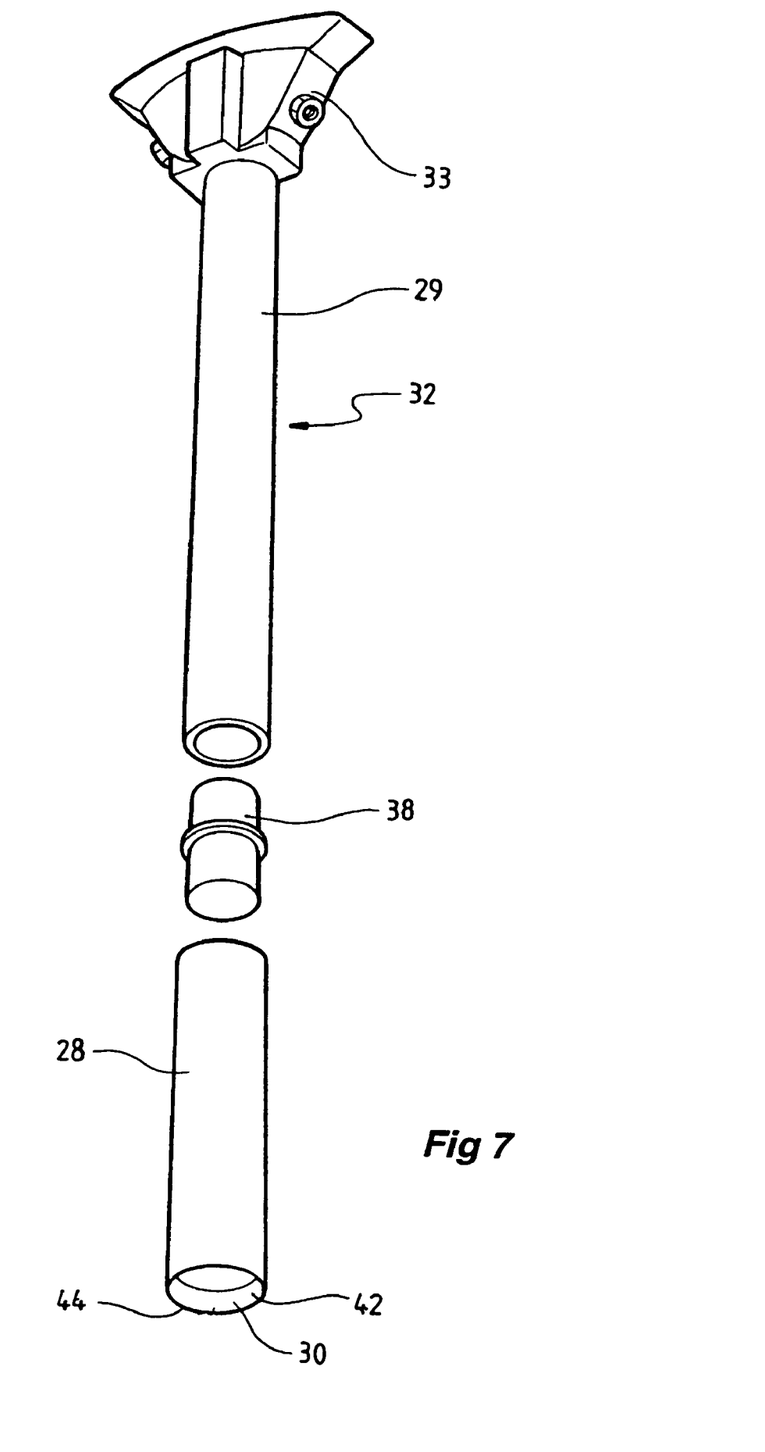
FIG. 7 depicts an embodiment of the invention that includes separated head and inserted ends before being joined.

The opening 30 in the base of the inserted end of the probe body 32 is adapted for ease of insertion into the prepared opening in the ground, by the provision of a chamfer 42 on the peripheral edge of the opening 30 as depicted in FIGS. 4, 5 and 7. This chamfer creates a knife like edge 44 that removes a portion (ideally an annular portion) of the soil about the prepared opening in the ground and directs the passage of soil into the lower chamber 34 upon it reaching the end of its travel into the prepared opening.

The cleaner the removal action of the chamfered edge on the soil, (42, 44) the more likely the interface between the surrounding soil and the outer surface of the probe body will be absent of air gaps when the probe body has been fully inserted.

The soil removed by the insertion process associated with the above-described slicing action can only fall into the lower portion of the prepared opening in the ground.

It is desirable that for most soils, the chamber 34 will be substantially occupied by removed soil but not so much as to provide any substantial resistance to the downward motion of the probe body 28 into the prepared opening in the ground.

The inner diameter X of the prepared opening in the ground is clearly less than the outer diameter Y of the probe, as shown in FIG. 4.

In one embodiment X is 28.5 mm which is conveniently the outer diameter of a commonly available hand operated soil auger of the type depicted in FIG. 2. The other dimension Y is 32 mm, which is the outer diameter of a custom sized ABS pipe that forms the elongate probe body.

Clearly, other dimensions would suffice as long as the volume of the annular soil sliced away creates a minimally compacted volume of soil at the bottom of the prepared opening in the ground, that fits into the inserted end chamber 34 of the probe.

In a preferred arrangement the length of the inserted end is approximately half the length of the head end of the probe body.

FIG. 5 depicts the probe at almost its deepest position and shown is the accommodation of minimally compacted soil occupying the chamber 34 in the inserted end of the probe body. The probe body is fully inserted following the removal of the stabilisation plates 20, which are separated after removal of the pins 20a and after removing the wing nuts that serve to join the two plates together at the join between the plates. Other plate fixing means possibly of the quick fix and release types are also envisaged.

Figure 6:
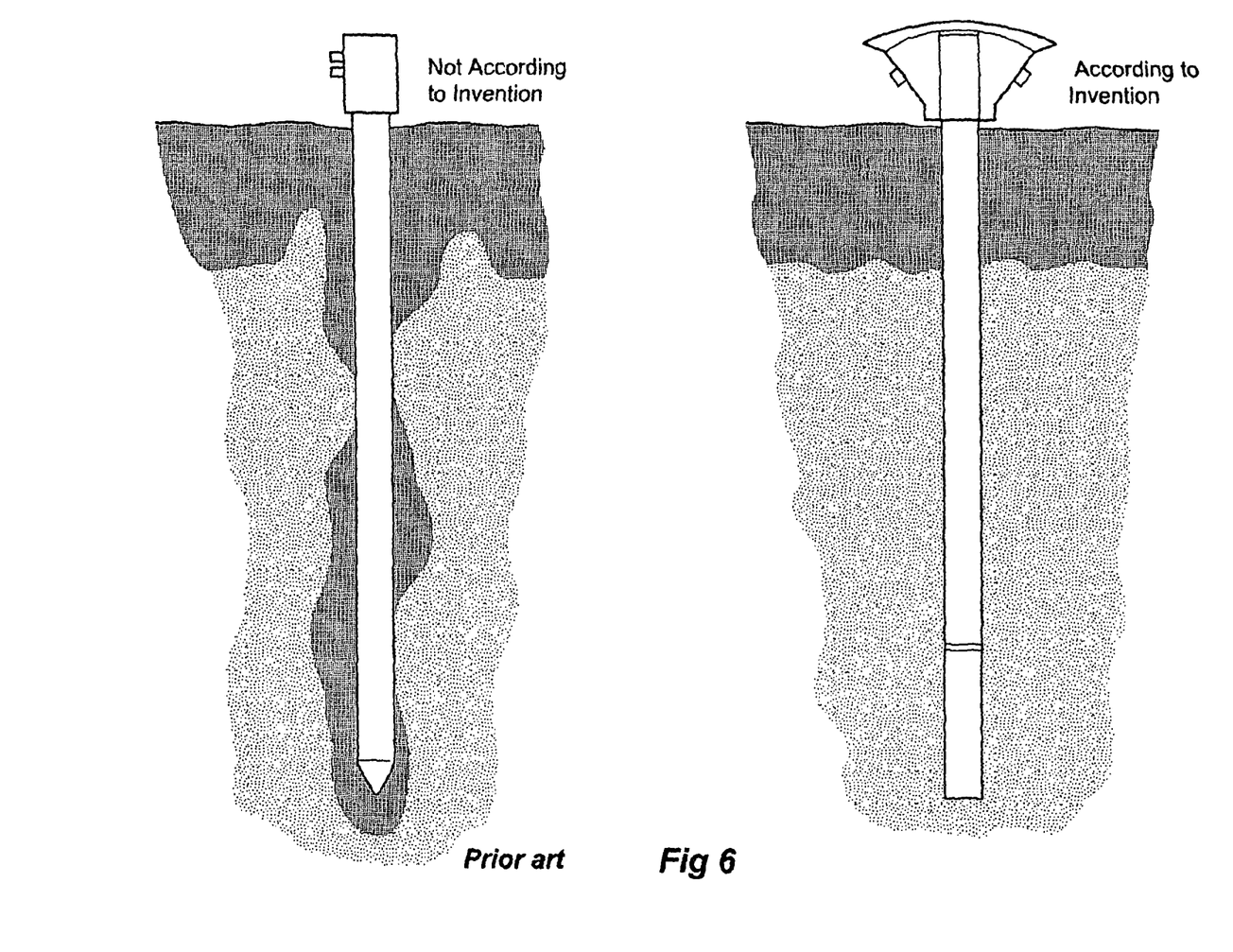
FIG. 6 depicts a side by side comparison of probe housing installed with and without the use of the method and apparatus of the invention.

The head of the probe body preferably lies adjacent to the top of the soil at full insertion as depicted in FIG. 6. The shape of the cap or head of the probe shown in FIG. 5 is immaterial but its construction should preferably be robust enough for it to be tapped with a hammer to assist with the insertion of the probe into the prepared opening (if necessary).

An alternative arrangement for assisting insertion is described later in the specification.

The electronic sensor array 18, that measure soil parameters are preferably inserted into the probe body after it has been placed in the soil. However, the devices that make up the sensor should also be robust enough to survive being inside the probe housing during its installation procedure.

FIG. 6 depicts examples from the field of a cross-sectional view of two sensor probe housings. The wetting pattern disclosed (darker area) is the result of infiltration of water into the soil surrounding each of the probe bodyies. It will be noted that the distribution of the water about the probe housing on the right is confined to the upper stratum of the surrounding soil. Whereas the distribution of the water about the probe housing on the left depicts preferential path flow of water in the vicinity of the probe housing well below the upper stratum. The distribution on the left shows pluming (lateral and downward migration of water) along its length as well as below, caused by the flow of water along an imperfect interface between the outer surface of the probe housing and the soil that is caused in the main by poor installation practice.

Such pluming will detrimentally affect sensor readings, resulting in incorrect representations of soil parameters being measured by the sensor equipment and consequently agronomic interpretation will be adversely affected.

FIG. 7 shows the three major parts of the probe body 32 in an exploded view suitable for fitment together. The head end 29 and inserted end 28 of the probe are connected with a joiner/barrier element 38.

This embodiment of the probe body clearly comprises three parts, but it could be possible to make such a body in one piece or indeed it could be made of more than three parts, as may be the case. It has been found however that since the probe body can be dismantled, this allows the inserted end 28 to be more easily emptied and cleaned of soil ready for reuse. Furthermore, if either end is damaged it can be replaced separate from the remaining end.

Figure 8:
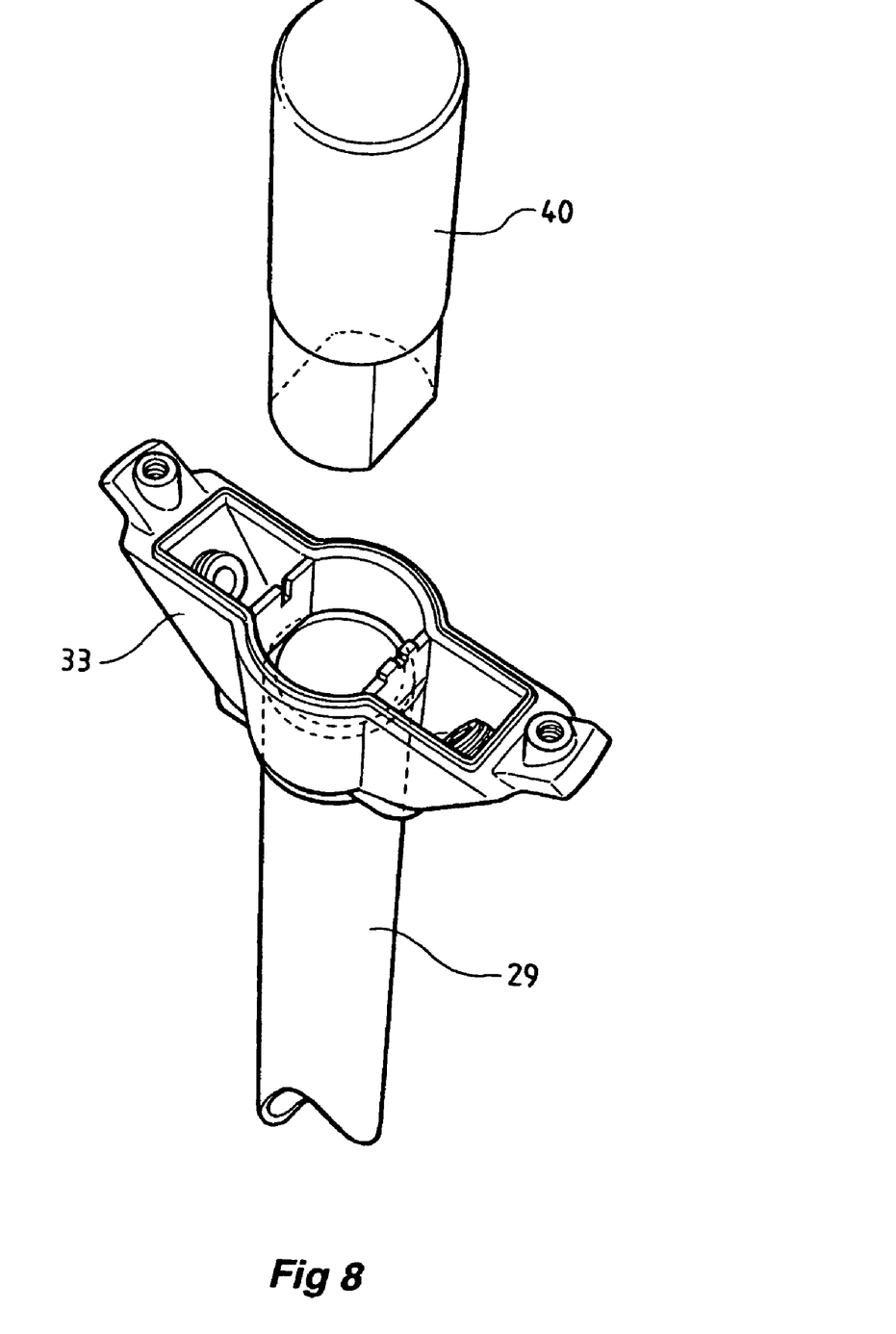
FIG. 8 depicts a perspective view of the open top of a probe housing and dolly ready for use in the installation process.

FIG. 8 depicts a perspective view of the top end of the probe body 29 and inside the probe body head 33. Also shown is a dolly 40 which is preferably made of impact resistant plastic. The lower portion of the dolly is shaped to fit into the probe body head. The lower portion is part circular and part parallel sided so as to allow a portion of the upper annular surface of the pipe that forms the elongate probe body to abut the bottom surface of the dolly.

If need be the upper surface of the dolly once fitted into the probe body head can be struck with a mallet or similar to force the probe body into the soil. The use of special dolly obviates the need to strike the probe body head directly thus minimising damage. The dolly shown in FIG. 8 is designed to strike the upper portion of the probe body but a longer dolly could be used to strike the barrier between chambers.

The preferred method of use of the apparatus is described above but another method involves the creation of a longitudinal opening in the ground without the use of a stabilisation means. The longitudinal opening created should have a cross-sectional dimension smaller than the probe housing to be inserted and the opening in the ground is approximately as deep as the length of the probe housing. The use of a heavy metal mallet to insert the soil auger into the ground is preferable as it results in a cleaner entry of the auger into the soil and less chance of deflections from the vertical as it creates an opening in the soil for the probe housing.

The depth of the opening in the ground can be slightly less than the length or slightly longer than the length of the probe body. It is possible in the case of a lesser length, for the opening of the inserted end of the probe body to penetrate unexcavated soil to ensure the probe body descends to the required depth.

Also it is possible in the case of a greater length for the opening of the inserted end of the probe body to come to rest above the bottom of the opening in the ground but for displaced soil to fill the void that would otherwise exist.

It will be appreciated by those skilled in the art, that the invention is not restricted in its use to the particular application described. Neither is the present invention restricted in its preferred embodiments with regard to the particular element and/or features described or depicted herein. It will be appreciated that various modifications can be made without departing from the principles of the invention. Therefore, the invention should be understood to include all such modifications within its scope.

The invention claimed is:

1. A body for insertion into a prepared opening in the ground consists of,
    an elongate body having a head end and an inserted end wherein said inserted end has a downwardly facing opening that is coaxial to said elongate body and that opens to a hollow portion of said elongate body and the outer diameter of the body is constant along the head and inserted ends wherein the prepared opening is smaller in outer diameter than the inserted end of the elongate body and wherein the downwardly facing opening is adapted for reaming said prepared opening using a slicing action so as to allow the head end to lie adjacent the ground surrounding the body and for soil to drop to the bottom of the prepared hole and at least a portion of the dropped soil entering the hollow portion of the elongate body when the body is positioned in the prepared opening, wherein said hollow portion is terminated along the length of the elongate body to form a head end chamber and an inserted end chamber in the body so that each chamber is physically isolated from the other.

2. A body according to claim 1 wherein the downwardly facing opening is adapted by being chamfered for ease of insertion into a prepared opening in the ground.

3. A body according to claim 1 wherein the peripheral edge of the downwardly facing opening is chamfered on its inside to create a sharp edge on the outside edge that in use remove a portion of the ground about the prepared opening in the ground such that the removed portion of the ground falls to the bottom of the prepared opening in the ground and which eventually enters the downwardly facing opening of the inserted end into the hollow portion of the elongate body.

4. A body according to claim 1 wherein fitting the inserted end to the head end of the probe body forms a portion of said elongate body.

5. A body according to claim 1 further comprising a body insertion stabilizing means positioned adjacent to the ground surface arranged to maintain the entry position of a tool that creates the opening in the ground during the creation of that opening and wherein said stabilization means is also adapted to maintain the entry position of the body as it is inserted into the prepared opening.

6. A body according to claim 5 wherein said probe insertion stabilising means comprises two separable parts secured to the ground by one or more pegs.

7. A method of inserting into the ground a body comprising the steps of
    a) creating a longitudinal opening in the ground having cross-sectional dimensions smaller that that of the body to be inserted and which is at least as deep as the length of said body to be inserted into the ground;
    b) inserting the inserted end of the body into the opening, said body having a hollow downwardly open portion adapted for removing a portion of the ground about the prepared opening using a slicing action as said body is inserted wherein said removed ground falls to the bottom of the prepared opening and enters the downwardly facing opening of the inserted end and the hollow portion of the elongate body until the required depth of the probe has been inserted, and
    c) positioning adjacent to the around surface a probe body insertion stabilising means that maintains the entry position of the tool that creates the opening in the ground during the creation of that opening and which is also adapted to maintain the entry position of the body as it is inserted into the prepared opening.

8. A method of inserting into the ground a body according to claim 7 further comprising the step of
    d) removing the probe body insertion stabilising means before the full insertion of the probe body so as to position the head end of the body as deep in said soil as adapted to do so.

* * * * *